United States Patent [19]

Wu et al.

[11] Patent Number: 4,534,781

[45] Date of Patent: Aug. 13, 1985

[54] MUSHROOM SUPPLEMENT CONTAINING PROTEIN AND A TIME DELAY COATING

[75] Inventors: Lung-chi Wu; Carl W. Bretzloff, both of Napoleon, Ohio

[73] Assignee: Campbell Soup Company, Camden, N.J.

[21] Appl. No.: 402,314

[22] Filed: Jul. 27, 1982

[51] Int. Cl.³ .............................................. C05F 11/00
[52] U.S. Cl. ........................................ 71/5; 71/64.02; 71/64.07; 47/57.6; 426/93; 426/132; 426/309
[58] Field of Search ....................... 71/5, 64.02, 64.07, 71/64.2, 64.7; 47/1.1, 57.6; 426/309, 93, 125, 132

[56] References Cited

U.S. PATENT DOCUMENTS

| | | | |
|---|---|---|---|
| 2,117,315 | 5/1938 | Gössel | 426/309 |
| 2,585,026 | 2/1952 | Moen et al. | 426/309 |
| 2,648,163 | 8/1953 | Szuecs . | |
| 2,898,214 | 8/1959 | Ferrel | 426/309 |
| 3,306,730 | 2/1967 | Malmberg et al. | 71/64.07 |
| 3,458,303 | 7/1969 | Belak et al. | 71/64.07 |
| 3,560,190 | 2/1971 | Hughes et al. . | |
| 3,744,987 | 7/1973 | Omura et al. | 71/64.07 |
| 3,903,333 | 9/1975 | Shirley, Jr. et al. | 71/64.07 |
| 3,942,969 | 3/1976 | Carroll, Jr. et al. . | |
| 4,042,366 | 8/1977 | Fersch et al. | 71/64.11 |
| 4,059,919 | 11/1977 | Green . | |
| 4,082,533 | 4/1978 | Wittenbrook et al. | 71/64.12 |
| 4,142,885 | 3/1979 | Heumann et al. | 71/64.07 |
| 4,333,757 | 6/1982 | Kurtzman, Jr. . | |
| 4,337,594 | 7/1982 | Hanacek et al. . | |
| 4,339,456 | 7/1982 | Rushing | 47/57.6 |
| 4,370,159 | 1/1983 | Holtz | 71/5 |
| 4,420,319 | 12/1983 | Holtz | 71/5 |
| 4,452,008 | 6/1984 | Sandhu et al. | 71/64.07 |

FOREIGN PATENT DOCUMENTS

| | | | |
|---|---|---|---|
| 4107543 | 8/1979 | Japan . | |
| WO82/00637 | 3/1982 | PCT Int'l Appl. | 47/1.1 |

OTHER PUBLICATIONS

Markley, *Soybeans and Soybean Products*, vol. 1 (1950), pp. 278–288, Interscience Publishers Inc., New York.

A. D. Carroll, Jr., "Improving Post-Composting Mushroom Supplements for use at Spawning", Master's Thesis, Aug. 1973.

*Primary Examiner*—D. E. Gantz
*Assistant Examiner*—Lance Johnson
*Attorney, Agent, or Firm*—Banner, Birch, McKie and Beckett

[57] ABSTRACT

An improved nutrient supplement is disclosed for enhancing the growth of mushroom mycelium in a compost bed comprising a particulate nutrient supplement having at least a partial coating of a hydrophobic material that is not readily assimilable by competing microorganisms in the compost.

20 Claims, No Drawings

MUSHROOM SUPPLEMENT CONTAINING PROTEIN AND A TIME DELAY COATING

TECHNICAL FIELD

This invention relates to the art of mushroom cultivation and specifically pertains to an improved nutrient source for promoting mushroom growth.

BACKGROUND ART

The basic procedure for commercially producing mushrooms involves an initial step of impregnating a suitably prepared compost with mushroom mycelia. This step is referred to as "spawning", and is generally done in a plurality of individual beds or trays to facilitate handling and to economize space. The compost provides the nutrients, e.g., amino acids, essential for mycelium growth. The compost is often prepared from a mixture of horse manure and straw suitably treated, according to well known procedures, to yield a final composition promotive of mushroom growth. The mycelium-impregnated compost is then allowed to develop under carefully controlled conditions of temperature and moisture, until the hyphae of the mycelium have permeated the compost. This process usually takes anywhere from two to three weeks. At this time, the mycelia-permeated compost is covered with a thin layer of soil or sand; peat is often used. This step is referred to as "casing", and the presence to this top layer causes the mushrooms to "flower", i.e., to form the fleshy fruiting body harvested as the product. It genrally takes about three weeks after the beds are cased for the first mushrooms to appear. After harvesting the first crop of mushrooms, the bed goes through another growth cycle in which additional mushroom fruits are produced. These growth cycles are referred to as "breaks", and a commercial compost bed generally undergoes three to five breaks before the compost becomes significantly depleted in essential nutrients. The compost is then discarded and the procedure is initiated anew.

The prior art has shown that enhanced mushroom yields can be obtained by adding supplementary nutrients to the compost bed. For example, in Hughes et al. U.S. Pat. No. 3,560,190 a dry formulation based on a combination of cottonseed meal and cottonseed oil is disclosed as a suitable supplement. It is also known to use cracked soybeans as a supplement, i.e., soybeans that have been broken into smaller pieces of about 1/6 to 1/10 the size of the whole bean. These materials have been added to the compost bed both at the time of spawning and casing.

Nutrient supplementation, however, is susceptible to some undesirable side effects. One problem that has been encountered is excessive bed heating, apparently caused by the ready availability of the nutrient source to the highly active microbial mushroom culture. Temperature excursions above 35° C. (95° F.), sufficient to significantly deplete, if not completely destroy the mushroom mycelia have been observed. Another problem is encountered when adding the supplement to the compost at the time of spawning. In many cases other micro-organisms, primarily molds, pre-existing in the compost, introduced with the supplement, or introduced via airborne contamination, compete with the mushroom mycelium for the added nutrients. This reduces the availability of the supplement for its intended purpose and often hinders the development of the mushroom mycelium.

Recognizing these problems, Carroll et al. U.S. Pat. No. 3,942,969 provides a supplement suitable for addition to the compost at the time of spawning, in which the release of the nutrient is delayed. This supplement comprises a denatured protein source, including proteins derived from cottonseed, soybean and peanuts. As disclosed, the denaturing can be accomplished by heating or by treatment with alkalies, acids or formaldehyde. Unfortunately, the potential gains in mushroom yields, are disadvantageously offset by the economic penalty associated with the denaturation treatment.

It is an object of the invention to provide a mushroom supplement for increasing the yield of mushrooms in commercial mushroom production.

It is another object of this invention to provide a mushroom supplement having a delayed release of nutrients for stimulating mycelium growth.

It is a further object of this invention to provide a mushroom supplement that can be added to the compost either at spawning or up to casing.

It is yet another object of this invention to provide a mushroom supplement that is more economical to produce than the denatured protein of Carroll et al.

DISCLOSURE OF THE INVENTION

These and other objects are met by the present invention which comprises an improved nutrient supplement for enhancing the growth of mushroom mycelium in a compost bed comprising a particulate, nutrient supplement having at least a partial coating of a hydrophobic material that is not readily assimilable by competing microorganisms in the compost, whereby the coating delays the availability of the nutrient to the mushroom mycelium while said coating is gradually removed under the conditions of mushroom growth. The present invention also pertains to a method of making the improved supplement and a method for using the supplement to enhance the growth of mushroom mycelium.

In another aspect of this invention, the hydrophobic coating may also include a component for inhibiting the growth of molds.

DETAILED DESCRIPTION

As disclosed, the present invention comprises a nutrient supplement for enhancing the growth of mushroom mycelium. By at least partially coating previously known nutrient supplements, such as cracked soybeans, with a thin layer of a hydrophobic material, such as a paraffin wax, we have found that commercial mushroom yields can be significantly enhanced while successfully avoiding the problems of excessive bed heating and competing microbial attack.

In the broadest aspects of this invention, the particulate nutrient supplement comprises any material which is known to beneficially enhance the growth of mushroom mycelium, i.e., materials which satisfy the function of a nutrient. Materials such as vitamins, minerals, proteins, carbohydrates, sugars, etc. can be employed. Protein-containing nutrients from both vegetable and animal sources are particularly useful. Specific sources of protein-containing nutrients include fish meals, malt sprouts, linseeds, sesame seeds, peanuts, safflower and sunflower seeds, rape seed and many others. Vegetable protein sources such as cottonseed, soybean and peanuts are particularly advantageous. Although the use of soybeans as the particulate nutrient supplement is specifically referred to throughout the specification, such other materials as described above can also be usefully employed.

Microbial activity on a substrate material, i.e., the supplement, generally requires a certain degree of hydration, and in fact most molds except certain Aspergilli, require substantial moisture content in order to flourish. Consequently, by applying the hydrophobic coating to the supplement we have eliminated an essential pre-condition for rapid attack by molds in the compost. The coating itself, however, must not be readily assimilable by the molds in the compost, otherwise the purpose of the coating is substantially abrogated. As used in describing the hydrophobic material, the phrase "not readily assimilable" means that the material does not promote as rapid a growth of a competing microbial colony as does the uncoated nutrient supplement.

Substances which in appropriate circumstances may be used as the coating material include natural resins, such as shellac, natural waxes, such as beeswax and paraffin waxes; oils, such as mineral oils; animal fats and synthetic low melting or solvent soluble polymers. Generally, the solid paraffin waxes are preferred. Relative to the waxes, the paraffin oils have been found to provide the supplement with less resistance to attack by molds. The vegetable oils such as safflower, cottonseed, soybean, corn, olive, linseed, rape seed, sesame, wheat germ, sunflower seed, and palm oil are known to be particularly subject to competing microbial attack and as such are preferably not used in the present invention, unless a component suitable for inhibiting mold growth to be described in more detail hereafter, is included in the oil coating. A mold inhibitor found to be suitable is benzoic acid.

When coating the supplement with a natural wax, for example, a paraffin wax, sized pieces of the raw supplement are first placed in a vessel equipped for heating and stirring. The supplement is initially pasteurized by heating the vessel to about 60° to 65° C. (140°-150° F.), while stirring the contents of the vessel. After an appropriate period at the pasteurization temperature, an appropriate amount of the paraffin wax, in molten form, is added to the vessel. A paraffin wax that can be processed at temperatures sufficiently low so as not to thermally degrade the nutrient is used. The contents of the vessel are cooled, accompanied by constant stirring, until the temperature falls below the congealing point of the wax. If necessary, an anti-caking agent, e.g., Celite, may be added to prevent the coated particulates from agglomerating.

While coating levels within the broad range of 2%-15% may be suitable in certain circumstances, we have found that coating levels between 4% and 11% yield the best results. As used in the specification and claims, the term "coating level" means the coating weight percent of a particular component based on the weight of the supplement substrate. For example, a paraffin wax coating level of 7% means that a quantity of paraffin wax coating material equal to 7% as the weight of the supplement substrate is applied as a coating. The lower limit of the coating level range is set by the need to suitably delay the availability of the substrate; while the higher limit should not be exceeded or else the supplement becomes essentially unavailable to the mushroom mycelium within the time frame typical of mushroom growth. High coating levels also present agglomeration problems during manufacture. The coating level to be used in any particular case depends upon a variety of factors including the point in the mushroom growing process when the supplement is added to the compost bed, and the severity of the mold problem associated with a particular compost. For example, a supplement applied at spawning time will generally require a higher coating level than one applied at casing time. The present invention also contemplates the addition of a supplement, or a combination of supplements, with different fractions having various coating levels. Current testing has shown that coating levels between about 4% and 9%, e.g., 7% are suitable for supplements applied at casing time, while coating levels between 7% and 11%, e.g., 10% are appropriate for supplements applied at spawning.

In practicing various embodiments of this invention, a compost suitable for promoting the growth of mushroom mycelium is initially prepared. Details of this procedure need not be elaborated as they are well understood by one skilled in this art. Tests have shown that the supplement of this invention is compatible with a wide variety of mushroom composts. Suitable materials for preparing the compost include: horse manure, straw, corn cob, and other vegetative waste materials. The trays to be used for growing the mushrooms are then filled with the compost and the compost is thereafter impregnated with the mushroom mycelia. A wide variety of mushrooms can benefit from the supplement of this invention, and the invention is not limited to any particular mushroom species or strain thereof.

As noted above, the supplement can be applied either at the time of spawning or up to the time of casing the compost bed. When applying the supplement at spawning, the particulate supplement will generally be admixed into the compost bed with the mycelia. This procedure eliminates the additional labor associated with applying the supplement at casing. The supplement is provided in a particulate form that allows it to be added to the compost bed using available spawning equipment. Soybeans cracked to about 1/6 to 1/10 the size of the whole beans have been found to be suitable.

The supplement is generally added to the bed at a rate of from 2% to 8% based on the dry weight of the compost in the bed. The rate of application in any particular case is based on a number of factors including: the supplement used, the mushroom variety and the compost formulation. As higher supplement application rates are used, the added mushroom yield per weight of added supplement decreases. Consequently, in any case there will be an economically defined upper limit for the supplementation rate.

The spawned compost beds are then allowed to develop under carefully controlled conditions until the mycelia have completely permeated the compost. The present invention does not require any special provisions, and conditions normally employed for growing mushrooms can be advantageously employed. This process will usually take about two to four weeks. The beds are then cased with a layer of soil or peat. If the supplement was not added at the time of spawning, it is done at this time. This is simply done by admixing the supplement into the compost bed prior to applying the layer of casing material. Generally, the first crop of mushrooms can then be harvested about three weeks after casing. The mushroom bed then goes through additional growth cycles in which additional mushrooms are produced. Generally, a commercial bed will undergo three to five such growth cycles before the compost is replaced.

As disclosed, the coating inhibits the growth of competing microorganisms on the supplement and delays the availability of the nutrient to the mushroom mycelium, while the coating is gradually removed under the conditions of mushroom growth. While we do not wish to be bound by theory, we believe that various microorganisms within the compost bed are capable of gradually breaking down the hydrophobic coating so as to gradually expose the nutrient supplement in a form suitable for assimilation by the mushroom mycelium. These microorganisms apparently comprise a portion of the organism population that survives the compost pasteurization step. While the compost is generally pasteurized to kill harmful pathogens, e.g., heating the compost for two to six hours at 60° to 65° C. (140°–150° F.) is typical, this treatment does not eradicate all of the organisms in the compost. For example, thermophilic and spore-forming microorganisms normally survive this treatment. Of the organisms surviving this treatment, there are apparently some capable of gradually degrading suitable hydrophobic coating materials, such as paraffin wax. Throughout the specification and claims the phrase "gradually removed under the conditions of mushroom growth" is used to describe this process, as well as any other contributing processes by which the coating is gradually removed from the supplement.

In another aspect of this invention, the hydrophobic coating material also includes an additional component for inhibiting the growth of molds. The mold inhibitor can be conveniently admixed with the coating material before it is applied onto the nutrient. For example, in the case where a molten paraffin wax is used to coat cracked soybeans, the particular mold inhibitor component can first be admixed into the molten wax. This mixture is then used to coat the soybeans according to the procedure described earlier. Other procedures for including a mold inhibitor in the coating will be apparent to one skilled in the art.

The suitability of a particular material as a mold inhibitor in a specific hydrophobic coating material of this invention can be verified by routine experimentation. We have found that benzoic acid applied at a coating level of 2% have been effective in suppressing mold growth to a suitable degree.

The following examples will illustrate various working embodiments of the present invention.

EXAMPLE I

In this example, the results of small scale pot testing are described in which cracked soybeans were used as a nutrient supplement. The hulls, fines and extraneous weed seeds were removed from the cracked beans, which were then sieved to yield pieces averaging about 30 mg in size (about $\frac{1}{8}$ of a whole bean). Various bean fractions were then coated with a variety of materials including beef tallow, clear shellac, orange shellac, beeswax and paraffin wax. All of the coatings were applied at a coating level of 5%, with the exception of one fraction which was coated with paraffin at 7%. In all, 10 samples were tested to determine their effect on mushroom growth.

The mushroom beds were prepared by adding 200 grams of compost, on a dry weight basis, having a 65% moisture content, to each pot. The pots were then spawned with mushroom mycelia of the species *Agaricus bisporus*. After allowing the mycelia suitable time to mature, the supplement was added to the pots and the compost beds were cased. Most of the supplements were added at a rate of 2%, although two samples, an orange shellac coated fraction and a clear shellac coated fraction, were applied at a rate of 6% and 8%, respectively. Six pots were prepared for each sample, with the exception of the clear shellac sample applied at a rate of 8% where only four pots were prepared because of a limited quantity of supplement material. Three breaks were obtained from each sample and the data are reported as the average total yield of the various replicates for each sample. An unsupplemented sample was used as a standard.

The results are presented in Table 1. As shown, the best results were obtained with the 7% paraffin coated sample, the orange shellac sample at a 6% supplementation rate and the clear shellac sample at an 8% supplementation rate, producing 29% 50% and 64% increase in yields, respectively. The samples prepared with beef tallow, paraffin wax at a 5% coating level, and the basic clear shellac and orange shellac coatings exhibited essentially no improvement relative to the unsupplemented sample in these tests. The clear and orange shellac samples in which the soybeans were soaked in 80% alcohol and the beeswax coated sample produced only marginal improvements of 9% and 17%, respectively.

TABLE 1

| SUPPLEMENT POT TESTING | |
|---|---|
| Coating | Yield (gram/pot) |
| Unsupplemented | 139 |
| Beef Tallow | 134 |
| Paraffin Wax | 137 |
| Clear Shellac | 141 |
| Orange Shellac | 148 |
| Clear Shellac[1] | 151 |
| Orange Shellac[1] | 151 |
| Beeswax | 162 |
| Paraffin Wax[2] | 180 |
| Orange Shellac[3] | 209 |
| Clear Shellac[4] | 228 |

[1] Soybeans preliminarily soaked in 80% alcohol
[2] 7% coating level
[3] 6% supplementation rate
[4] 8% supplementation rate

EXAMPLE II

This example presents the results of testing in which five different composts were used to examine the effect of a paraffin coated, cracked soybean supplement on mushroom growth. The soybeans were prepared in the manner described in Example I and were then coated at various levels with a paraffin wax by the procedure described earlier. Coating levels of 6%, 7%, 8% and 9% were tested.

The same mushroom strain employed in Example I was used for these tests. These tests were also conducted in pots, provided with 200 grams of compost on a dry basis. The mushroom beds were supplemented at casing at four different rates: 2%, 3%, 4% and 5%. Consequently, a total of 16 supplemented samples were tested for each compost. Additionally, an untreated sample was also prepared using each of the five composts to serve as a standard.

The results are presented in Table 2 as the weight of mushrooms produced in a supplemented tray per unit weight of mushrooms produced on the unsupplemented composts. The entry at each coating level represents an average of the yields obtained at the four supplementation rates tested. The results indicate that yield increases from 13% to 203% were observed. Overall the supplement increased the mushroom yields an average of 50%. Based on the weight of supplement applied, an overall average of 7.0 grams of mushrooms were produced for each gram of supplement used.

TABLE 2

RELATIVE MUSHROOM YIELDS

| Compost | Coating Level (%) | | | | |
|---|---|---|---|---|---|
| | 6 | 7 | 8 | 9 | Ave. |
| WS104 (Syn. 4) | 1.27 | 1.26 | 1.20 | 1.21 | 1.23 |
| Brighton HM65 | 2.03 | 1.82 | 1.79 | 1.65 | 1.82 |
| Glenn HM70 | 1.49 | 1.37 | 1.30 | 1.38 | 1.38 |
| Jackson HM | 1.90 | 1.87 | 1.83 | 2.03 | 1.90 |
| GH101 (Syn. 1) | 1.24 | 1.18 | 1.21 | 1.13 | 1.19 |

EXAMPLE III

A number of tests were conducted in which a wide variety of soybeans were examined for their effect on mushroom growth. All of the soybeans were prepared in the manner described in Example I, and were coated with paraffin wax at a coating level of 7% using the procedure described earlier.

The same mushroom strain employed in Example I was used in these tests. The tests were also conducted in pots, each provided with 200 grams of compost on a dry basis. As in the previous examples, the mushroom beds were supplemented at casing at a rate of 4%. An unsupplemented sample was also prepared to serve as a standard.

The results are listed in Table 3. The data are presented as the 25 day percent conversion which is the weight of mushrooms produced

TABLE 3

RELATIVE MUSHROOM YIELDS USING VARIOUS SOYBEAN VARIETIES

| Variety | 25 Day Converstion (%) |
|---|---|
| AgriPro 250 | 125 |
| Shawnee-11 | 120 |
| SRF150 | 119 |
| RS 2300 | 119 |
| Gnome | 119 |
| Wayne | 117 |
| Beeson | 117 |
| Shawnee | 115 |
| SRF 307-P | 113 |
| Pilla | 111 |
| Wells 11-254 | 110 |
| AgriPro 26 | 108 |
| Williams 79 | 108 |
| AgriPro 27 | 108 |
| Williams | 107 |
| Amsoy 71-211 | 107 |
| Peterson 4880 | 107 |
| Asgrow 3127 | 106 |
| Vickery | 106 |
| AgriPro 25 | 104 |
| Washington V | 103 |
| Corsoy | 101 |
| Unsupplemented | 81 | per unit weight of dry compost in 25 days. This corresponded to three mushroom breaks. Improvements between 25% and 54% over the unsupplemented sample were obtained. These results indicate that this invention can be used to prepare a wide range of soybean varieties as mushroom supplements.

EXAMPLE IV

This example presents results obtained when using a paraffin coated soybean supplement at spawning time. The soybeans were preliminarily treated in the manner described in Example I and were then coated at the 7%, 9% and 11% levels with a paraffin wax according to the procedure described earlier.

The same mushroom strain used in the earlier examples was also employed in these tests. These tests were also conducted in pots provided with 200 grams of compost on a dry basis. The mushroom beds were supplemented at spawning at a rate of 6%. An untreated sample was also prepared as the standard.

The results are illustrated in Table 4. The data are presented as the percent conversion after 28 days. Conversion improvements between 11% and 17% were observed.

TABLE 4

SUPPLEMENTATION AT SPAWNING

| Coating Level (%) | 28 Day Conversion (%) |
|---|---|
| 7 | 109 |
| 9 | 104 |
| 11 | 110 |
| Unsupplemented | 94 |

EXAMPLE V

This example describes results obtained using paraffin wax-coated soybean supplements. Five different grades of paraffin waxes were tested. The soybeans were initially prepared in the manner described in Example I and were then coated at four different coating levels, i.e., 4%, 5%, 6% and 7%, using the various waxes. The procedures described earlier for coating soybeans with a paraffin wax were used.

The same mushroom strain employed in earlier test work was used again. The tests were conducted in pots provided with 200 grams of compost on a dry basis. The mushroom beds were supplemented at casing at a rate of 4%. An unsupplemented sample was also prepared for comparison.

The results are presented in Table 5 as the weight of mushrooms produced in a supplemented tray per unit weight of mushrooms produced in the unsupplemented tray. The data indicate that yield increases from 36% to 54% were obtained. These results show that a variety of paraffin waxes can be successfully used to coat the supplement.

TABLE 5

RELATIVE MUSHROOM YIELDS

| Paraffin Wax* | Coating Level (%) | | | | |
|---|---|---|---|---|---|
| | 4 | 5 | 6 | 7 | 8 |
| SR 125 q | 1.42 | 1.41 | 1.39 | 1.38 | 1.41 |
| FR 131 q | 1.45 | 1.50 | 1.53 | 1.52 | 1.48 |
| FR 335 M | 1.52 | 1.45 | 1.45 | 1.45 | 1.47 |
| MICRO 155 | 1.42 | 1.42 | 1.36 | 1.38 | 1.39 |
| MICRO 175 | 1.41 | 1.39 | 1.35 | 1.54 | 1.41 |

*Obtained from:: Walnut-Hill, Inc., Green Lane and Wilson Ave., P.O. Box 599, Bristol, PA 19007

EXAMPLE VI

In this example, the use of a component for inhibiting the growth of molds in the hydrophobic coating is described. Soybean supplements, preliminarily treated according to the procedure of Example I, were coated with paraffin wax at a coating level of 7%. Various amounts of benzoic acid were included in the molten wax and applied with the coating as a mold inhibitor. Mushroom mycelia of the species *Agaricus bisporus* were spawned into compost beds, which were then subsequently supplemented at casing with the above-prepared supplements at a 4% supplementation rate. Relative to an unsupplemented standard, these supplements improved the conversion after three breaks between 22% and 55%. More importantly, microbiological analysis showed that at a coating level of benzoic acid of 2% and above, mold growth was completely inhibited.

While certain specific embodiments of the invention have been described with particularity herein, it will be recognized that various modifications thereof will occur to those skilled in the art. Therefore, the scope of the invention is to be limited solely by the scope of the appended claims.

We claim:

1. An improved nutrient supplement for enhancing the growth of mushroom mycelium in a compost bed comprising a particulate primarily non-denatured protein-containing nutrient supplement having a coating of a hydrophobic material that is not readily assimilable by competing microorganisms in the compost, which coating delays the availability of the nutrient to the mushroom mycelium while said coating is gradually removed under the conditions of mushroom growth.

2. The nutrient supplement of claim 1 wherein said particulate nutrient supplement has a hydrophobic material coating level of from 2% to 15%.

3. The nutrient supplement of claim 2, suitable for mixing into said compost bed at the time of spawning of the mycelium, wherein said particulate nutrient supplement has a hydrophobic material coating level of from 7% to 11%.

4. The nutrient supplement of claim 2, suitable for mixing into said compost bed at the time of casing said bed, wherein said particulate nutrient supplement has a hydrophobic material coating level of from 4% to 9%.

5. The nutrient supplement of claim 1 wherein the hydrophobic material is selected from the group consisting of paraffin wax and shellac.

6. The nutrient supplement of claim 1 wherein said protein-containing nutrient is cracked soybean.

7. A process for making an improved primarily non-denatured protein-containing nutrient supplement for enhancing the growth of mushroom mycelium in a compost bed comprising:
   (a) providing a primarily non-denatured protein-containing nutrient supplement in particulate form suitable for addition to the compost bed;
   (b) pasteurizing said nutrient; and
   (c) applying a coating of a hydrophobic material, to said nutrient, which coating delays the availability of the nutrient to the mushroom mycelium while said coating is gradually removed under the conditions of mushroom growth, said hydrophobic coating being not readily assimilable by competing microorganisms in the compost.

8. A process according to claim 7 wherein the hydrophobic material is a molten wax and wherein after step (c) the coated nutrient is cooled below the congealing point of said wax.

9. The process of claim 7 wherein a hydrophobic material coating level of from 2% to 15% is applied to said particulate nutrient supplement.

10. The process of claim 9 for making a nutrient supplement suitable for mixing into said compost bed at the time of spawning of the mycelium, wherein a hydrophobic material coating level of from 7% to 11% is applied to said particulate nutrient supplement.

11. The process of claim 9 for making a nutrient supplement suitable for mixing into said compost bed at the time of casing said bed, wherein a hydrophobic material coating level of from 4% to 9% is applied to said particulate nutrient supplement.

12. The process of claim 7 wherein the hydrophobic material is selected from the group consisting of paraffin wax and shellac.

13. The process of claim 7 wherein said protein-containing nutrient is cracked soybean.

14. A method for enhancing the growth of mushroom mycelium in a compost bed comprising admixing into said compost either at the time of spawning of the mycelium or up to the time of casing the compost bed an effective amount of a particulate primarily non-denatured protein-containing nutrient supplement having a coating of a hydrophobic material that is not readily assimilable by competing microorganisms in the compost, which coating delays the availability of the nutrient to the mushroom mycelium while said coating is gradually removed under the conditions of mushroom growth.

15. The method of claim 14 wherein said particulate nutrient supplement has a hydrophobic material coating level of from 2% to 15%.

16. The method of claim 15 wherein said particulate nutrient supplement has a hydrophobic material coating level of from 7% to 11% and said supplement is mixed into said compost bed at the time of spawning of the mycelium.

17. The method of claim 15 wherein said particulate nutrient supplement has a hydrophobic material coating level of from 4% to 9% and said supplement is mixed into said compost bed at the time of casing said bed.

18. The method of claim 14 wherein the hydrophobic material is selected from the group consisting of paraffin wax and shellac.

19. The method of claim 14 wherein said protein-containing nutrient is cracked soybean.

20. The method of claim 14 wherein the particulate nutrient supplement is added to said compost bed at a supplementation rate of from 2% to 8%.

* * * * *